(12) United States Patent
Gill

(10) Patent No.: US 7,931,608 B2
(45) Date of Patent: Apr. 26, 2011

(54) PEDIATRIC SPLINT

(76) Inventor: Jana B. Gill, Boise, ID (US)

( * ) Notice: Subject to any disclaimer, the term of this patent is extended or adjusted under 35 U.S.C. 154(b) by 337 days.

(21) Appl. No.: 12/090,091

(22) PCT Filed: Oct. 14, 2006

(86) PCT No.: PCT/IB2006/053780
§ 371 (c)(1),
(2), (4) Date: Apr. 12, 2008

(87) PCT Pub. No.: WO2007/043029
PCT Pub. Date: Apr. 19, 2007

(65) Prior Publication Data
US 2008/0228120 A1 Sep. 18, 2008

Related U.S. Application Data

(60) Provisional application No. 60/726,634, filed on Oct. 14, 2005.

(51) Int. Cl.
*A61F 5/00* (2006.01)
(52) U.S. Cl. ............................... 602/21; 602/5; 602/20
(58) Field of Classification Search .......... 602/5, 20–23, 602/30, 62–63; D24/190, 191; 128/877–879
See application file for complete search history.

(56) References Cited

U.S. PATENT DOCUMENTS

| | | |
|---|---|---|
| 1,375,690 A | 4/1921 | George |
| 1,817,212 A | 8/1931 | Siebrandt |
| 2,022,883 A | 12/1935 | Gee |
| 2,273,028 A | 2/1942 | Eaton |
| 2,523,606 A | 9/1947 | Young |
| 2,548,378 A | 4/1951 | Kleinfeld |
| 2,667,868 A | 2/1954 | Smyth |
| 2,957,475 A | 6/1958 | Drake |
| 3,039,460 A | 5/1959 | Chandler |
| 3,774,242 A | 11/1973 | Owen |
| 3,938,510 A | 2/1976 | Gerber |
| 4,549,537 A | 10/1985 | Ender |
| 4,657,000 A | 4/1987 | Hepburn |
| 4,873,968 A | 10/1989 | Finnieston |
| 5,101,812 A | 4/1992 | Wang |
| 5,197,943 A | 3/1993 | Link |

(Continued)

OTHER PUBLICATIONS

PCT International Search Report and Written Opinion for International Application No. PCT/IB2006/053780 dated Apr. 20, 2007.

*Primary Examiner* — Kim M Lewis
(74) *Attorney, Agent, or Firm* — Lisa K. Kennedy

(57) ABSTRACT

A splinting device for receiving and stabilizing a plurality of fingers. The splinting device has a main body having a generally rigid and planar upper surface and lower surface, a first side edge and a second side edge, a distal end portion and a proximal end portion. The main body has a hood at its distal end portion upending proximally over the upper surface of the main body. The hood has an upper surface and a lower surface, and the lower surface of the hood and the upper surface of the main body define an interior space for receiving a plurality of fingers. In one embodiment, the splinting device also includes a glove portion comprising a wrist attachment and a flap. The main body may comprise an attachment mechanism for attaching the main body to the wrist attachment of the glove portion.

15 Claims, 6 Drawing Sheets

U.S. PATENT DOCUMENTS

| | | |
|---|---|---|
| 5,230,699 A | 7/1993 | Grasinger |
| 5,267,945 A | 12/1993 | Doctor et al. |
| 5,554,076 A | 9/1996 | Clark |
| 5,730,154 A | 3/1998 | DeRidder |
| 5,925,008 A | 7/1999 | Douglas |
| 5,947,915 A | 9/1999 | Thibodo |
| 6,102,878 A | 8/2000 | Nguyen |
| 6,514,222 B2 * | 2/2003 | Cook ............... 602/21 |
| 6,561,995 B1 | 5/2003 | Thibodo, Jr. |
| 6,575,925 B1 | 6/2003 | Noble |
| 2005/0027223 A1 | 2/2005 | Nguyen |

* cited by examiner

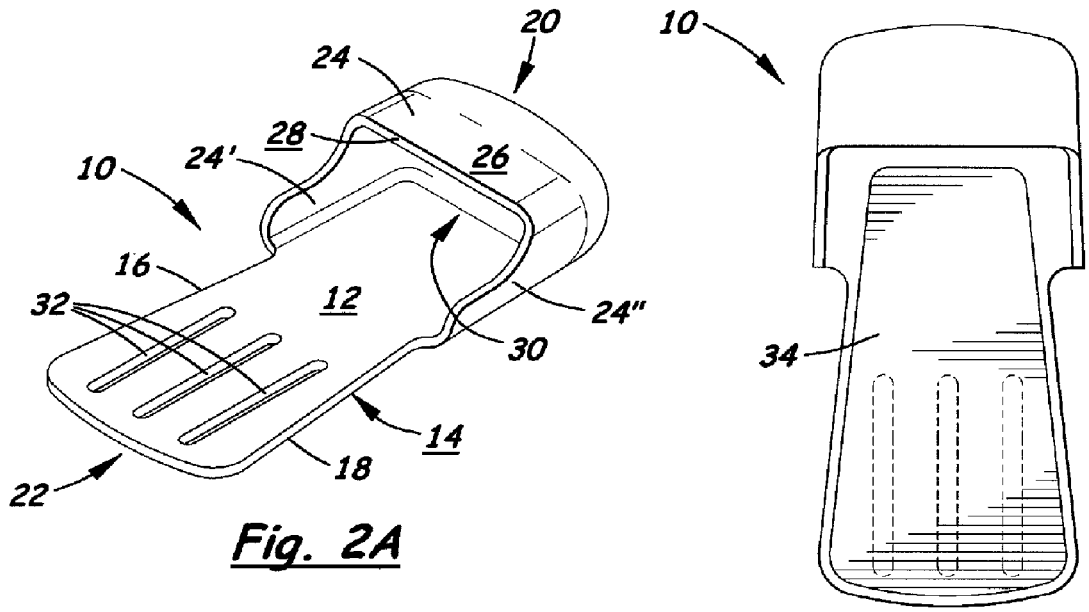
Fig. 2A
Fig. 2B
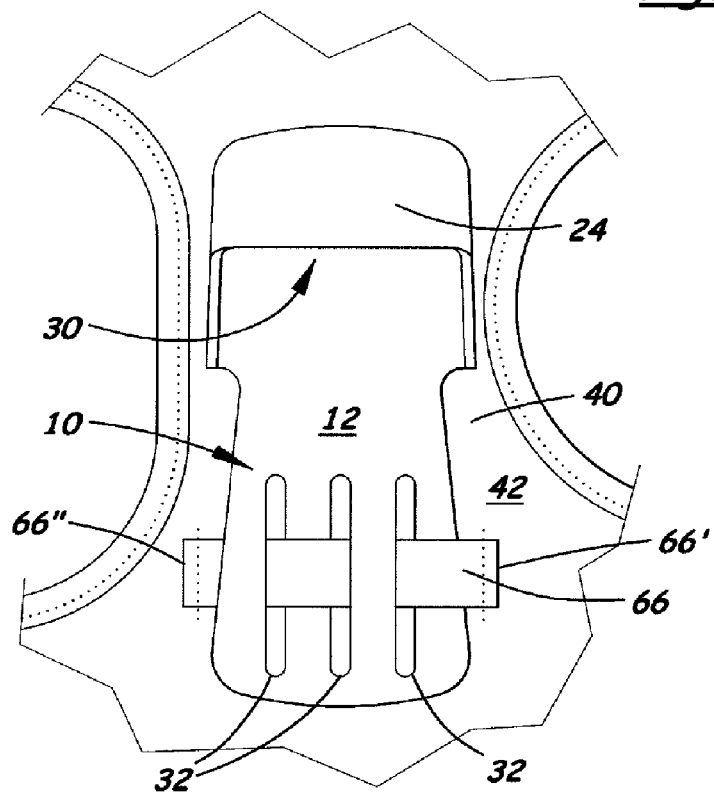
Fig. 2C

PEDIATRIC SPLINT

This application claims priority from PCT Application No. IB2006/053780, filed on Oct. 14, 2006, entitled "Pediatric Splint," which claimed priority from U.S. Provisional Patent Application Ser. No. 60/726,634, filed on Oct. 14, 2005, entitled "Pediatric Splint," the disclosures of which are incorporated herein by this reference.

BACKGROUND OF THE INVENTION

1. Technical Field

The present disclosure relates to an orthopedic splinting devices, and, more specifically, to a finger splint for children.

2. Description of Related Art

Injuries to fingers and hands are common in children under the age of 5. Some studies show that in the United States, finger injuries account for approximately two-thirds of hand injuries in children. Many injuries in preschool age children are caused by fingers being jammed or crushed in doors. As children get older, finger injuries may result from recreational activity. It can be difficult to treat finger injuries in children due to the small size of their hands and their high activity level. Some children find immobilization of their fingers frustrating and will not leave a splint on for the entire duration of their treatment due to the lack of comfort and its interference within their daily activities.

Common finger injuries include ligament injuries, tendon injuries, sprains, strains, fractures, dislocations, lacerations, avulsions, amputations, or a combination of any of the above. Each finger or phalanx, except the thumb, contains three bony segments (the distal, middle, and proximal phalanx) and three joints which permit bending (flexion) and straightening (extension) of the fingers. The joint between the distal phalanx and the middle phalanx is called the distal interphalangeal joint, the joint between the middle phalanx and the proximal phalanx is called the proximal interphalangeal joint, and the joint between the proximal phalanx and the metacarpal bone is the metacarpophalangeal joint.

A common ligament injury to the finger(s) occurs at the proximal interphalangeal joint. The proximal interphalangeal joint is held together by ligaments, called collateral ligaments, which traverse the joint and attach to the bony segments on either side of the joint. The collateral ligaments of the proximal interphalangeal joint may be injured by a bending or twisting mechanism. When the finger is struck by an object and forced to one side or the other the collateral ligaments may tear resulting in a sprain of the collateral ligaments. Partial tears or sprains of the collateral ligaments are typically treated using a method known as "buddy-taping". The injured finger is taped to a normal adjacent digit. The tape is worn continuously for a period, such as three weeks, and then for an additional three weeks during periods of anticipated activity. The current method of buddy-taping, with standard cloth tape available in most emergency departments and drug stores, often does not hold up to persistent activity. The tape may fall apart and children tend to remove the tape because it is inconvenient and uncomfortable. The tape tends to get caught in the creases of the fingers becoming very uncomfortable. Parents may try splinting the finger(s) with a stiff bulky material, such as an emery board, which quickly becomes a nuisance for the child and they remove it.

Volar plate injuries may be caused by hyperextension of the proximal interphalangeal joint, and is usually associated with dorsal dislocation of the middle finger. Typical treatment involves closed reduction of the dislocation which anatomically realigns the avulsed ligaments. A dorsal splint is placed on the finger to prevent hyperextension and lateral stresses. A dorsal splint can be difficult to put on a child due to the small size of their fingers and their tendency to remove the splint because it is uncomfortable.

A mallet injury results from an injury to the extensor tendon which is distal to the proximal interphalangeal joint resulting in the inability to flex the distal interphalangeal joint. Due to the small size of children's hands it can be difficult to place a splint on the distal portion of the injured finger or fingers.

A crush injury to the tip of the finger(s) causes one of the most common fractures in children, often resulting from the finger(s) getting caught in a door. Crush injuries may be treated with a foam aluminum splint. However, these splints can be too bulky for a child's finger, and children may remove the splint prior to the end of treatment. Additionally, single-finger splinting may be difficult to maintain even in an adolescent.

Other splinting systems may be very complex, expensive and may be adapted to highly specific finger injuries. Additionally, these splints are not well adapted to be placed on a child's hand because they are complicated to put on and do not accommodate their small fingers. Devices such as the ulnar gutter splint and the volar splint are often bulky and uncomfortable, and children tend to remove the splint prior to the end of the treatment period.

Therefore, there is still a need for a finger splint for use with children that: easily allows the combined splinting of two or more adjacent fingers at one time with a single device; can accommodate small hands; is comfortable to wear for long periods of time; may accommodate open or closed wounds on the fingers; is easy to take on and off; or, is durable to withstand the high activity level of a child.

DISCLOSURE OF INVENTION

The present invention relates generally to splinting devices, and more specifically, to a splinting device for children. The splinting device is adapted to receive a plurality of fingers for stabilization and protection as a result of an injury.

The splinting device comprises a generally planar, rigid main body portion for stabilizing a plurality of fingers. The main body comprises a hood at its distal end upending proximally over the upper surface of the main body. The lower surface of the hood and the upper surface of the main body define an interior space for receiving and protecting the distal portions of two or more fingers.

In some embodiments, the main body also comprises an attachment mechanism at its proximal end for attaching to a glove portion. The glove portion comprises a wrist attachment for securing the glove portion and main body of the splinting device to the hand. Additionally, the glove portion comprises a flap which acts as a "butterfly" bandage over the fingers and main body. The flap may be removably attached to the wrist attachment or they may be a single unit.

BRIEF DESCRIPTION OF THE SEVERAL VIEWS OF THE DRAWINGS

FIG. 2A is a perspective view of a main body of a splinting device.

FIG. 2B is a plan view of the embodiment shown in FIG. 2A.

FIG. 2C is a partial plan view of the embodiment shown in FIGS. 2A and 2B with the main body secured to a wrist attachment of a glove portion of the splinting device.

DETAILED DESCRIPTION OF THE INVENTION

Referring to the Figures, there are shown several, but not the only embodiments of the invented pediatric splint. In this Description and the Claims, the term "proximal" means toward the center/torso of the body, whereas the term "distal" indicates a point farther from the center/torso of the body. Other directional or anatomical terms of reference used herein are "anterior" meaning toward the front; "volar" meaning the front or anterior surface of the hand; "posterior" meaning toward the back; "dorsal" meaning the back or posterior surface of the hand; "medial" or "ulnar" surface of the hand meaning inwardly from the side toward the midline of the body or the side where the pinkie is positioned; "lateral" or "radial" surface of hand meaning outwardly from the midline of the body toward the side or the side on which the thumb is positioned; "abduction" is movement of a body part away from the longitudinal axis of the limb; and, "adduction" is movement of a body part toward the longitudinal axis of the limb.

In order to visualize the structural arrangement of the hand, it may be divided into three fundamental planes of reference: a sagittal plane, a coronal plane, and a transverse plane (see FIG. 7 for an example of the sagittal, coronal and transverse planes in reference to one embodiment of the splinting device 100). A sagittal plane extends vertically through the hand dividing it into lateral and medial portions. A coronal plane also passes lengthwise and divides the hand into anterior and posterior portions. A transverse plane divides the hand into proximal and distal portions.

Figure 1A:
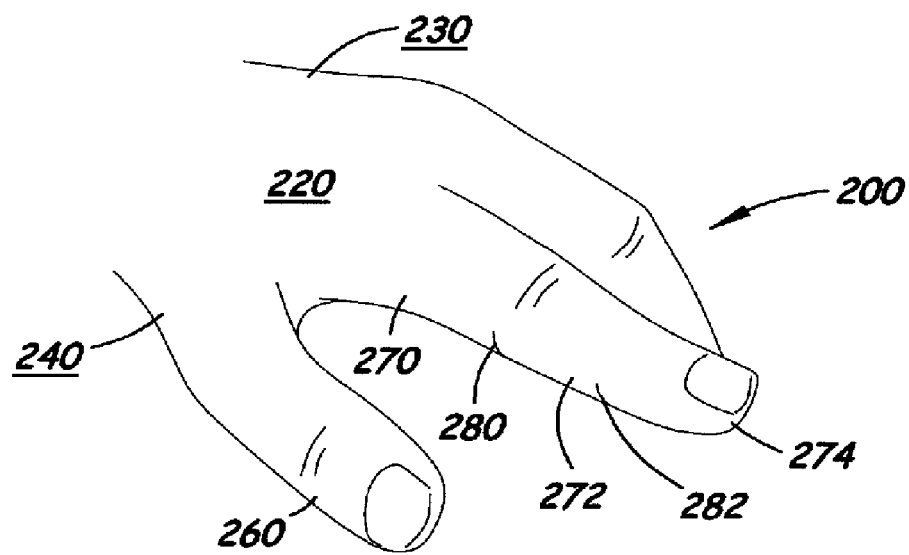
FIGS. 1A and 1B are illustrations of a left hand.
Figure 1B:
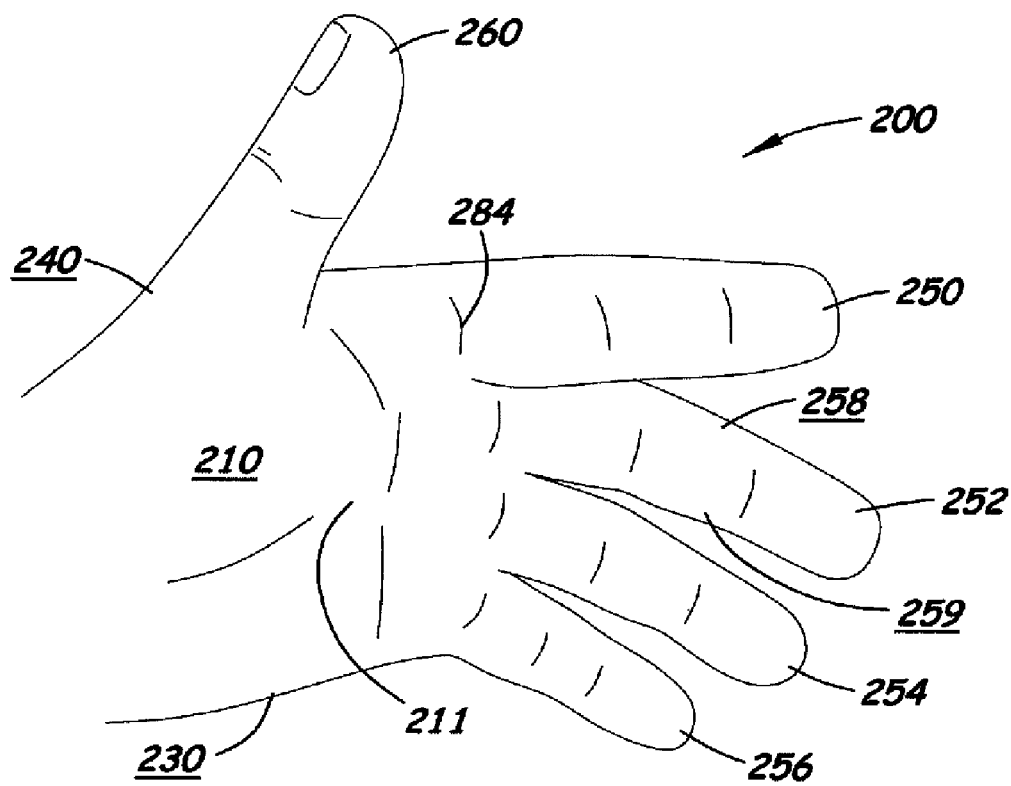

The hand 200 comprises three principal divisions: the carpus, or wrist; the metacarpus, containing the metacarpal bones; and the five digits (see FIG. 1B), a thumb 260 and four fingers (index 250, middle 252, ring 254 and pinkie 256). As shown in FIGS. 1A and 1B, the anterior portion of the hand 200 is referred to as the volar surface 210, and the posterior portion of the hand 200 is referred to as the dorsal surface 220. The palm 211 of the hand 200 is located on the volar surface 210 of the hand 200. The hand 200 also comprises a lateral, or radial surface 240 and a medial, or ulnar surface 230. Each finger (250, 252, 254, and 256) also has a lateral surface 258 and a medial surface 259. The fingers (250, 252, 254, and 256) each include three bones called phalanges: the proximal 270, middle 272 and distal 274 phalanges. Between the middle 272 and distal 274 phalanx of a finger is a distal interphalangeal joint 282 and between the proximal 270 and middle 272 phalanx of a finger is a proximal interphalangeal joint 280. Between the proximal phalanx 270 and palm 211 is the metacarpophalangeal joint 284. Terms of direction that describe the relationship of the hand 200 to the preferred embodiment of the splinting device 100 are made in reference to anatomical position. In anatomical position, the arms are at the sides of the body with the palms of the hands turned forward and the fingers pointed straight down.

Figure 3A:
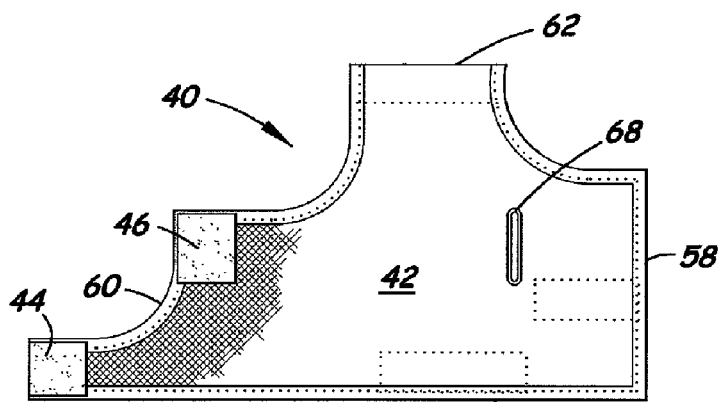
FIG. 3A is a plan view of an interior surface of a left-handed wrist attachment of the glove portion of the splinting device.
Figure 3B:
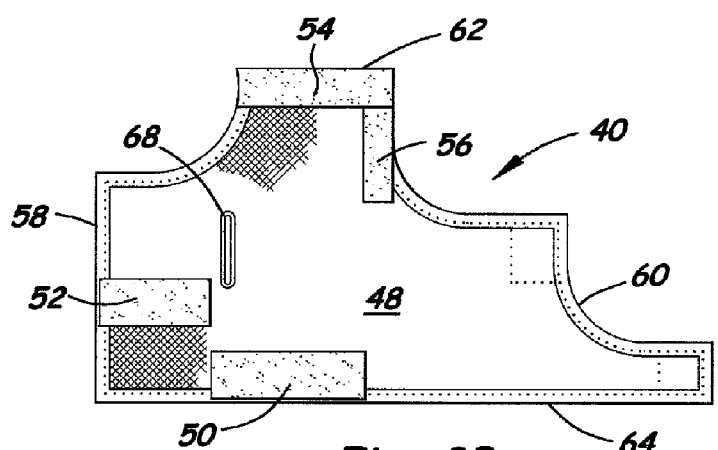
FIG. 3B is a plan view of the exterior surface of the embodiment shown in FIG. 3A.
Figure 4A:
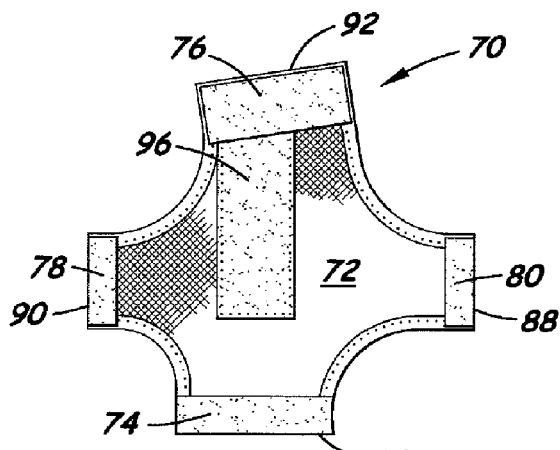
FIG. 4A is a plan view of the interior surface of a left-handed flap of the glove portion of the splinting device.
Figure 4B:
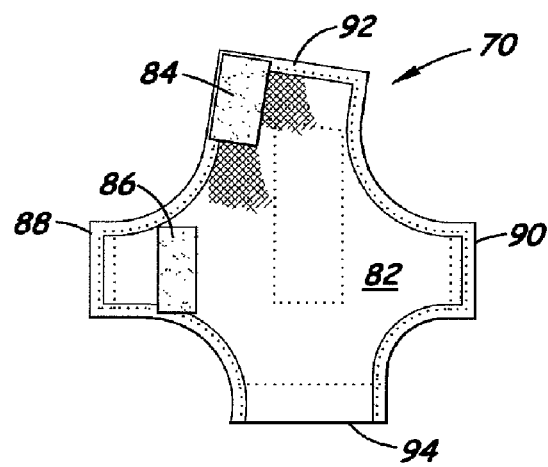
FIG. 4B is a plan view of the exterior surface of the embodiment shown in FIG. 4A.

In one embodiment, the splinting device 100 comprises a main body 10 (see FIGS. 2A-2B), and a glove portion 150 (see FIGS. 5 and 6); the glove portion 150 includes a wrist attachment 40 (see FIGS. 3A and 3B) and a flap 70 (see FIGS. 4A and 4B). The main body 10 or "finger tray" is adapted to receive 2 or more fingers (250, 252, 254, or 256) depending on how many fingers are injured. The wrist attachment 40 secures the main body 10 to the fingers (250, 252, 254, or 256) and hand 200, while the flap 70 acts as a "butterfly" bandage around the fingers to protect the fingers from debris and/or further injury.

As shown in FIG. 2A, one embodiment of the main body 10 comprises an upper surface 12, a lower surface 14, a first side edge 16 and a second side edge 18, a distal end portion 20 and a proximal end portion 22. The upper 12 and lower 14 surfaces of the main body 10 are substantially planar and rigid in order to stabilize one or more fingers (250, 252, 254, or 256). The upper 12 and lower 14 surfaces may be slightly curved to mimic the naturally curvature of the volar surface 210 of the fingers (250, 252, 254, or 256). The thickness of the main body 10 may vary, but is preferably between 1/32"-1/8" thick, so that it is not too bulky.

The distal end portion 20 of the main body 10 comprises a hood 24, or ridge. The hood 24 comprises an upper surface 26, a lower surface 28, and two side walls 24' and 24". The hood 24 upends proximally over the upper surface 12 of the main body 10 to protect the fingers (250, 252, 254, or 256). The lower surface 28 of the hood 24 and the upper surface 12 of the main body 10 define an interior space 30 for receiving a plurality of fingers (250, 252, 254, or 256). For example, if the index 250 and middle 252 fingers of a left hand are injured, the distal ends of the fingers 250, 252 are inserted into the interior space 30, so that lateral surface 258 of the index 250 finger and the medial surface 259 of the middle 252 finger are near the side walls 24' and 24" of the hood 24. The volar surfaces 210 of the fingers 250, 252 are in contact with the upper surface 12 of the main body 10. Therefore, abduction and adduction movement of the fingers 250, 252 is prevented by the side walls 24' and 24" of the hood 24, and flexion and extension of the fingers 250, 252 is prevented by the hood 24 and the main body 10.

In an example embodiment, the hood 24 extends over the upper surface 12 of the main body 10 approximately a quarter of the length of the main body 10, and the side walls 24' and 24" extend approximately a third of the length of the main body. However, the side walls 24' and 24" of the hood 24 may be extended further along the length of the side edges 16 and 18 of the main body 10 to further prevent abduction and adduction movement of the fingers 250, 252, and the hood 24 may be extended further over the upper surface 12 of the main body 10 to further prevent flexion and extension of the fingers. The length of the main body 10 preferably extends past the metacarpophalangeal joint 284 into the palm 211 of the hand 200 so that the proximal 280, distal 282, and metacarpophalangeal 284 joints of the fingers (250, 252, 254, or 256) are stabilized and may rest comfortably on the main body 10 without the main body 10 irritating the creases of the joints (280, 282, and 284). The main body 10 and hood 24 may be manufactured of a rigid material, preferably a hard plastic; however, other substantially rigid materials may be used, in order to stabilize and immobilize the fingers (250, 252, 254, or 256) by preventing movement while at the same time providing enough room between the fingers and the main body 10 and hood 24 to allow for swelling.

As shown in FIG. 2B, the upper surface 12 of the main body may be manufactured to include a liner 34 to act as a padding for the fingers (250, 252, 254, or 256) and to absorb any blood or fluids that may result from an injury or open wound to the volar surface 210 of the fingers. The liner 34 is parallel to the upper surface 12 of the main body 10 and contacts a substantial portion of the upper surface 12 of the main body 10. The liner 34 may be attached to the upper surface 12 of the main body 10 with a permanent adhesive or other attachment means which secure the liner to the upper surface 12 of the main body 10. The liner 34 may be manufactured from a polyether/polyurethane blend medical foam; however, other cushioning material including those that are breathable, durable with water, and/or filter blood and/or air may be used. In one embodiment, the liner 34 may be removable, so that is attached to the upper surface 12 of the main body 10 with a removable adhesive; therefore, the liner 34 can be changed for cleaning or replaced with a new liner if the liner 34 becomes saturated or other impurities make the liner 34 unsanitary.

In an example embodiment, the upper surface 12 of the main body 10 may comprise a ramp descending from the upper surface 12 of the main body 10 so that the injured fingers (250, 252, 254, or 256) are flexed or bent toward the volar surface 210 of the hand 200. Alternatively, the main body 10 may comprise a ramp ascending the upper surface 12 of the main body 10 so that the injured fingers (250, 252, 254, or 256) are extended or bent away from the volar surface 210 of the hand 200. These embodiments may be helpful during the healing process in order to insure that the healed finger will be straight.

The main body 10 may comprise an attachment mechanism for attaching the main body 10 to the wrist attachment 40 of the glove portion 150. The attachment mechanism may be one or more elongated slots 32, as shown in FIGS. 2A-2C, at the proximal end portion 22 of the main body 10. The elongated slots 32 extend through the main body 10 of the splinting device 100 from the upper surface 12 of the main body 10 to the lower surface 14, and the elongated slots 32 are substantially parallel to the first 16 and second 18 side edges of the main body 10. As shown in FIG. 2C, the main body 10 may be attached to the wrist attachment 40 via a strap 66. The strap 66 comprises a first end portion 66' and a second end portion 66" as shown in FIG. 2C. The strap 66 is threaded through at least one of the elongated slots 32 and is attached to the interior surface 42 of the wrist attachment 40 at the first end portion 66' and second end portion 66". The strap 66 may be attached using stitching, adhesive, or other securement means. The strap 66 may be a continuous elastomeric band to allow the main body 10 to pivot about the strap 66. In other embodiments, the attachment mechanism may be adhesive, a snap, or a lock or other attachment mechanisms which secure the lower surface 14 of the main body 10 to the interior surface 42 of the wrist attachment 40. In an example embodiment, the length of the slots 32 are approximately 1⅛", the length of the strap is approximately 2", and the width of the strap is ¾"; however, the inventor envisions any number of lengths and widths may be used so long as the main body 10 may pivot about the attachment mechanism relative to the wrist attachment 40.

The splinting device 100 comprises a glove portion 150 that substantially covers the hand 200 and fingers (250, 252, 254, or 256), while leaving the thumb 260 exposed. The glove portion 150 comprises a wrist attachment 40 which is configured to secure the main body 10 of the splinting device 100 on the fingers (250, 252, 254, or 256) and hand 200. As shown in FIGS. 3A and 3B, the wrist attachment 40 comprises an interior surface 42, which substantially covers the volar 210 and dorsal 220 surfaces of the hand 200 when placed on the hand 200, and an exterior surface 48, which is exposed to the external environment. The wrist attachment 40 further comprises a first edge 58, a second edge 60, a distal end portion 62, and a proximal end portion 64. The wrist attachment 40 includes an opening 68 near the first edge 58 for receiving the thumb 260.

The wrist attachment 40 comprises a plurality of fasteners for securing the main body 10 and wrist attachment 40 to the hand 200. In one embodiment, the interior surface 42 of the wrist attachment 40 comprises a first fastener 44 and a second fastener 46 (see FIG. 3A). The first fastener 44 is positioned near the second edge 60 and proximal end portion 64 of the wrist attachment 40. The second fastener 46 is positioned near the second edge 60, but more distal than the first fastener 44. The exterior surface 48 of the wrist attachment 40 comprises a first fastener 50, a second fastener 52, a third fastener 54, and a fourth fastener 56. After the injured fingers (250, 252, 254, or 256) are placed in the main body 10 and the thumb 260 is inserted in the opening 68, the first fastener 44 on the interior surface 42 of the wrist attachment 40 is secured to the first fastener 50 on the exterior surface 48 of the wrist attachment 40. This secures the main body 10 to the fingers (250, 252, 254, or 256) and hand 200. In an alternative embodiment, the wrist attachment 40 may simply be a strap attached to a piece of material that is only the width of the main body 10; therefore, the wrist attachment 40 would not cover a substantial portion of the hand 200.

In another embodiment, the glove portion 150 further comprises a flap 70, or "covering", which is configured to secure the fingers (250, 252, 254, or 256) in the main body 10 and protect either open or closed wounds on the dorsal surface 220 of the fingers (250, 252, 254, or 256) and hand 200. As shown in FIGS. 4A and 4B, the flap 70 comprises an interior surface 72, which covers the upper surface 26 of the hood 24 and the dorsal surface 220 of the fingers (250, 252, 254, or 256) when placed on a hand 200, and an exterior surface 82, which is exposed to the external environment. The flap 70 generally resembles the shape of a plus sign or cross wherein there is a vertical portion and a transverse portion. The transverse portion of the flap 70 comprises a first wing 88, a second wing 90, and the vertical portion of the flap 70 comprises a top end portion 92, and a bottom end portion 94. The flap 70 may comprise a liner 96 to protect the dorsal surface 220 of the fingers (250, 252, 254, or 256) from further injury and to absorb any blood or fluids that may result from an injury or open wound to the dorsal surface 220 of the fingers. The liner 96 may be manufactured from a polyether/polyurethane blend medical foam; however, other cushioning material that is breathable, durable with water, and/or filters blood and/or air may be used.

The flap 70 comprises a plurality of fasteners for cooperating with the fasteners on the wrist attachment 40. As shown in FIG. 4A, the interior surface 72 of the flap 70 comprises a first fastener 74 near the bottom end portion 94 of the flap 70, a second fastener 76 near the top end portion 92 of the flap 70, a third fastener 78 near the second wing 90 of the flap 70, and a fourth fastener 80 near the first wing 88 of the flap 70.

Figure 5:
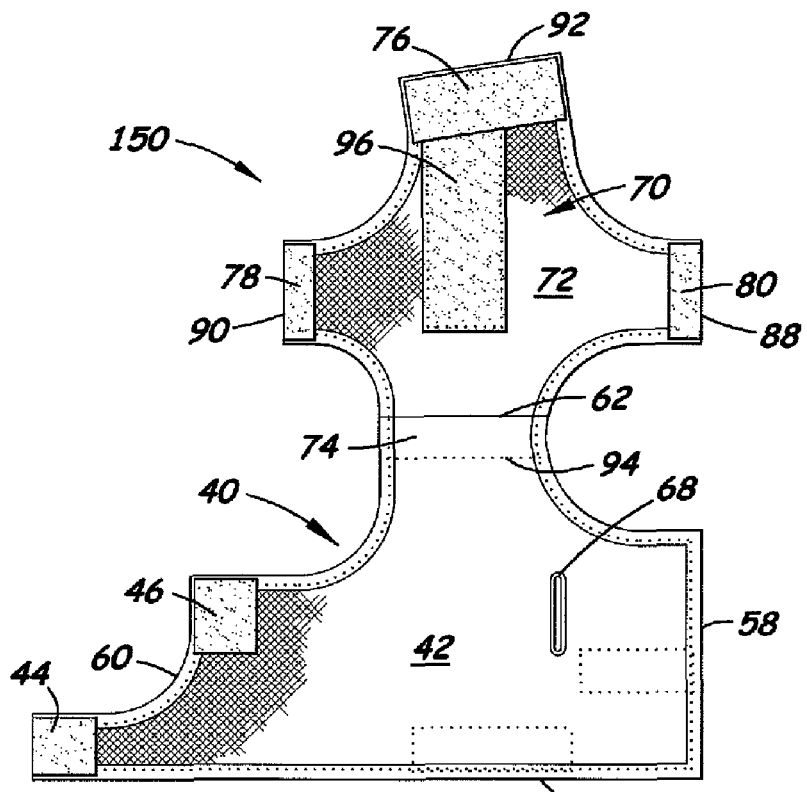
FIG. 5 is a plan view of the interior surface of the left-handed wrist attachment and flap of the glove portion of the splinting device shown in FIGS. 3A-4B, wherein the wrist attachment and flap are separate pieces and linked together with a fastener.
Figure 6:
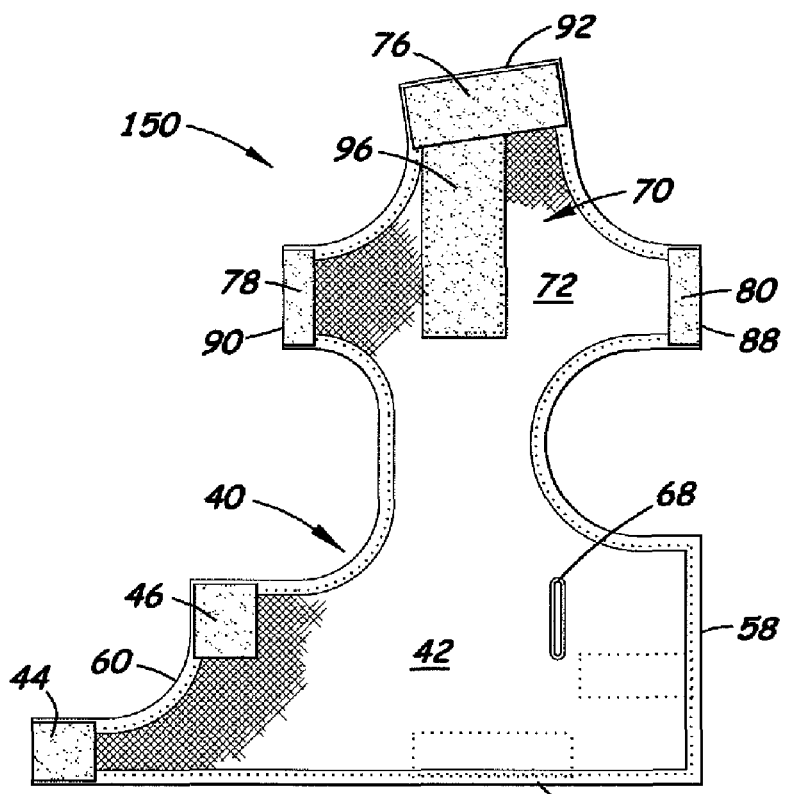
FIG. 6 is a plan view of the interior surface of the left-handed wrist attachment and flap of the glove portion of the splinting device shown in FIGS. 3A-4B, wherein the wrist attachment and flap are shown as a single unit.

The flap 70 may be used for either open wounds (where the skin is torn, cut or punctured and more prone to infection by bacteria) or closed wounds (a bruise that damages the underlying tissue without breaking the skin) on the dorsal surface 220 of the fingers (250, 252, 254, or 256). If there are open wounds on the dorsal surface 220 of the fingers (250, 252, 254, or 256) then the flap 70 may need to be removable, and preferably disposable, in order to change the dressing if the liner 96 and/or flap 70 become saturated or other impurities make the liner 96 and/or flap 70 unsanitary. In an example embodiment, as shown in FIG. 5, the flap 70 is releasably attached to the wrist attachment 40 via the flap fastener 74 and the fourth fastener 56 (shown in FIG. 3B), which may be referred to as a wrist fastener. The flap fastener 74 and fourth fastener/wrist fastener 56 may be hook-and-loop fasteners, such as Velcro®, snaps or other releasable fasteners. The flap 70 may be removed from the wrist attachment 40 and disposed of or cleaned, and a cleaned or new flap 70 may be placed back on the wrist attachment via the flap fastener 74 and the fourth fastener/wrist fastener 56. If the flap 70 is used for closed wounds then the flap 70 and wrist attachment 40 will normally be manufactured as one unit (see FIG. 6) without the need for fasteners 74 (on the flap 70) and 56 (on the wrist attachment 40).

In some embodiments, the glove portion 150 of the splinting device, including the wrist attachment 40 and the flap 70, may be manufactured out of any material that is, for example, comfortable to wear for long periods of time, antimicrobial to prevent infection of any open wounds, or moisture wicking and quick drying to handle spills and perspiration; for example, Innova AMP® is a material having many of these properties. The fasteners on the wrist attachment (44, 46, 50, 52, and 56) and flap (74, 76, 78, 80, 84 and 86) may be hook-and-loop fasteners, such as Velcro®, or alternatively, snaps, buttons, or any other fastener that secures the splinting device on the fingers (250, 252, 254, or 256) and hand 200. Additionally, the inventor contemplates that the fasteners may be positioned in different locations on the splinting device.

Figure 7A:
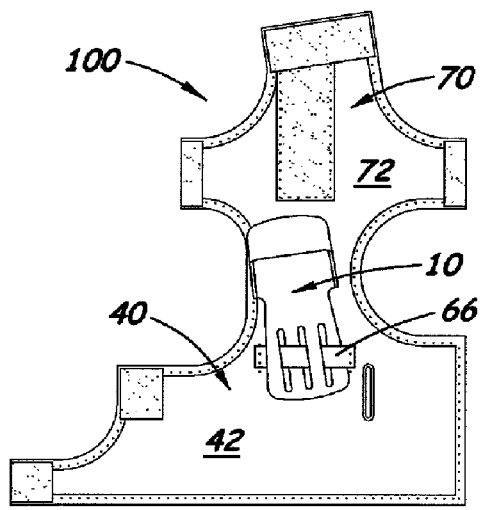
FIG. 7A is a plan view of a left-handed splinting device, wherein the main body is positioned to receive a ring and a pinkie finger of a left hand (hand not shown).
Figure 7B:
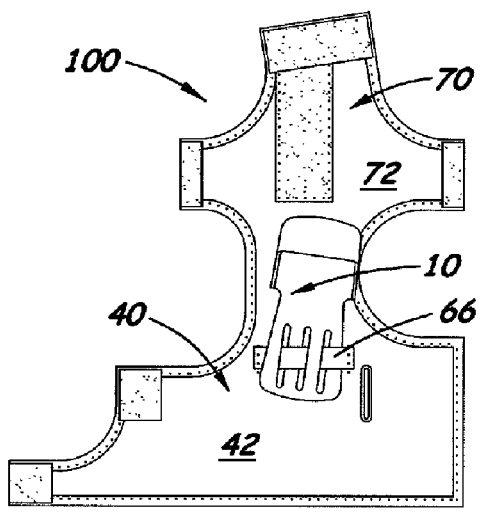
FIG. 7B is a plan view of a left-handed splinting device, wherein the main body is positioned to receive an index and a middle finger of a left hand (hand not shown).
Figure 8A:
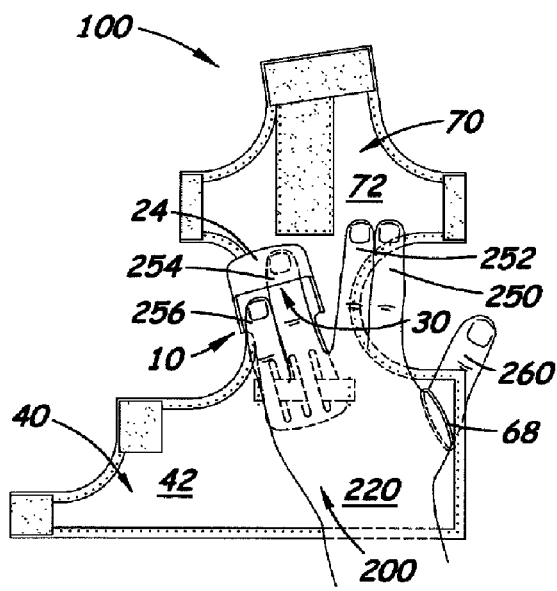
FIG. 8A is a plan view of the embodiment shown in FIG. 7A illustrating the ring finger and pinkie finger of the left hand inserted into the main body of the splinting device.
Figure 8B:
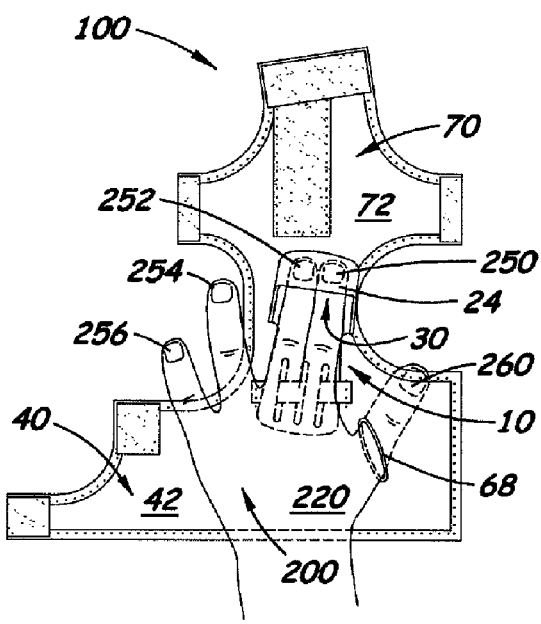
FIG. 8B is a plan view of the embodiment shown in FIG. 7B illustrating the index finger and middle finger of the left hand inserted into the splinting device.

In FIGS. 7A and 7B and 8A and 8B, a left-handed embodiment of the splinting device 100 is shown wherein the wrist attachment 40 and flap 70 are manufactured as one unit. As shown in FIGS. 7A and 7B, the main body 10 may pivot about the strap 66 which attaches the main body 10 to the wrist attachment 40. When the main body 10 is pivoted the strap 66 slides in the elongated slots 32. In the left-handed embodiment of the splinting device 100 illustrated, when the main body 10 pivots away from the thumb opening 68 it can receive the ring 254 and pinkie 256 fingers (see FIG. 7A). When the main body 10 pivots toward the thumb opening 68 it can receive the middle 252 and index 250 fingers (see FIG. 7B). The main body 10 may also be manufactured to accommodate two or more fingers (250, 252, 254, or 256). In an alternative embodiment, the main body 10, may be manufactured to accommodate a single finger.

Figure 9:
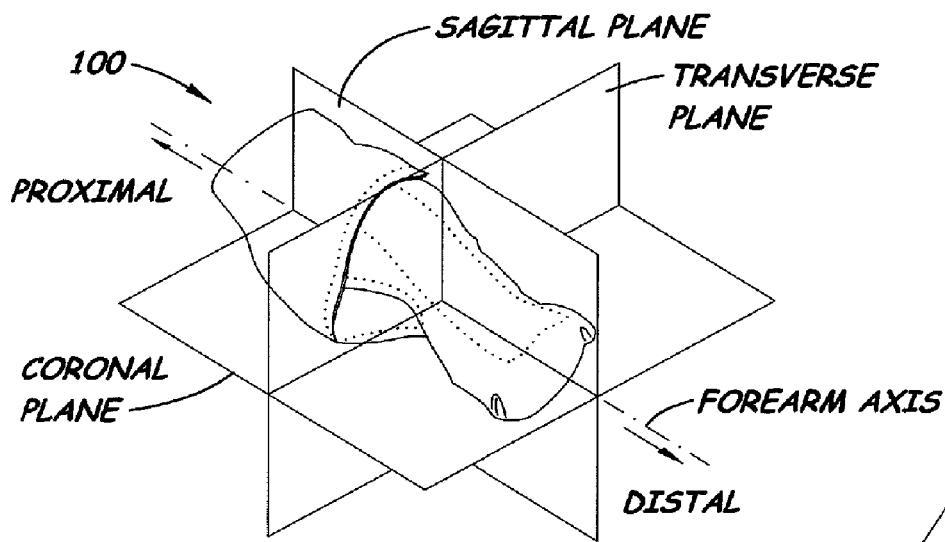
FIG. 9 is a schematic illustration of one embodiment of the left-handed splinting device with the various planes of an arm interposed thereon.
Figure 10:
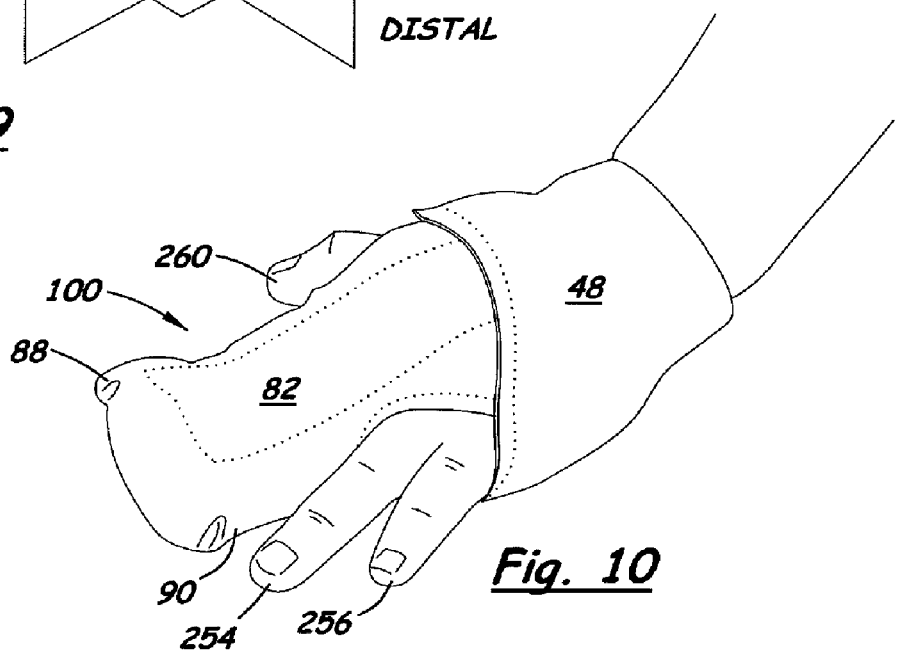
FIG. 10 is a posterior (dorsal) view of the embodiment shown in FIG. 9 on the left hand.
Figure 11:
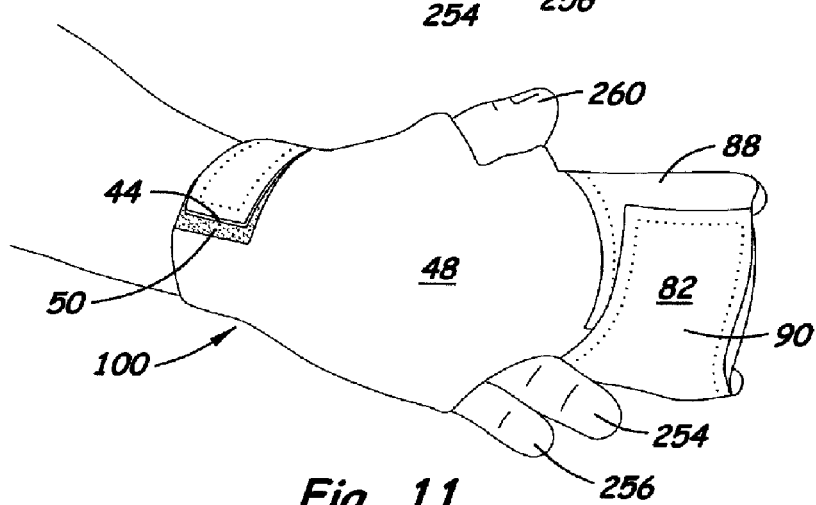
FIG. 11 is an anterior (volar) view of the embodiment shown in FIG. 9 on the left hand.

After the injured fingers (250, 252, 254, or 256) are placed in the main body 10 and the thumb 260 is placed in the opening 68, the wrist fastener 44 is attached to wrist fastener 50. If flap 70 is removable, then flap fastener 74 is attached to wrist fastener 56. Flap fastener 76 is then attached to wrist fastener 54. Flap fastener 76 is then attached to wrist fastener 52 covering the fingers (250, 252, 254, or 256) and main body 10. Wrist attachment 46 is then attached to flap attachment 84. In order to secure the wings 88 and 90 of the flap 70 around the injured fingers (250, 252, 254, or 256) like a "butterfly" bandage, flap fastener 80 attaches to wrist fastener 56 and flap fastener 78 attaches to flap fastener 86 wrapping the wings 88 and 90 around the fingers (250, 252, 254, or 256) from the dorsal surface 220 of the hand 200 to the volar surface 210 of the hand 200. Alternatively, the flap fastener 76 may be attached to the wrist fastener 52 first, then wrist fastener 44 is attached to wrist fastener 50 and wrist fastener 46 attaches to flap fastener 84. As shown in FIGS. 8 and 9, the glove portion 150 (including the wrist attachment 40 and flap 70) may cover a substantial portion of the hand 200, so that only the fingers not inserted in the main body 10 (250, 252, 254, or 256) and the thumb 260 are visible.

The splinting device 100 may be adapted to receive a plurality of fingers (250, 252, 254, or 256) for stabilizing and healing after an injury to the hand 200. The splinting device 100 may be manufactured to fit either a left or a right hand. The splinting device 100 may be manufactured in a variety of sizes to accommodate different size hands. For example, the inventor envisions having a small, medium and large size at a minimum. The small size may be in the range of 0.75"-1.25" wide, 1.5"-2.5" long, and the height of the hood 24 may be 0.25"-0.75" high. The medium size may be in the range of 1.25"-2" wide, 2.5"-3.5" long, and the height of the hood 24 may be 0.5"-1.0" high. The large size may in the range of 2"-4" wide, 3.5"-6.5" long, and the height of the hood 24 may be 0.75"-1.25" high.

Although this invention has been described above with reference to particular means, materials and embodiments, it is to be understood that the invention is not limited to these disclosed particulars, but extends instead to all equivalents within the scope of the following claims.

The invention claimed is:

1. A splinting device comprising:
a main body having an upper surface and a lower surface, a first side edge and a second side edge, a distal end portion and a proximal end portion;
the main body further comprising a hood at said distal end portion upending over a proximal portion of said upper surface of the main body;
wherein said hood comprises an upper surface and a lower surface, and wherein the lower surface of the hood and the upper surface of the main body define an interior space configured to receive at least two fingers;
a glove portion comprising a wrist attachment and a flap, the wrist attachment and flap each having an interior surface and an exterior surface;
wherein said interior surface of said wrist attachment is connected to the lower surface of the main body at said proximal end portion;
wherein said proximal end portion of the main body comprises one or more elongated slots extending through the main body from the upper surface of the main body to the lower surface of the main body, and wherein said one or more elongated slots are substantially parallel to said lateral and medial edges of the main body and perpendicular to said distal and proximal end portions, wherein a strap threadably engages said one or more elongated slots and said strap is connected to the interior surface of the wrist attachment.

2. A splinting device comprising:

a main body having an upper surface and a lower surface, a first side edge and a second side edge, a distal end portion and a proximal end portion;

the main body further comprising a hood at said distal end portion upending over a proximal portion of said upper surface of the main body;

wherein said hood comprises an upper surface and a lower surface, and wherein the lower surface of the hood and the upper surface of the main body define an interior space configured to receive at least two fingers;

a glove portion comprising a wrist attachment and a flap, the wrist attachment and flap each having an interior surface and an exterior surface;

wherein said interior surface of said wrist attachment is connected to the lower surface of the main body at said proximal end portion, wherein said wrist attachment further comprises:

a first edge and a second edge;

a first fastener on said exterior surface of the wrist attachment near said first edge; and a first fastener on said interior surface of the wrist attachment near said second edge, wherein said first fastener on the interior surface of the wrist attachment releasably attaches to said first fastener on the exterior surface of the wrist attachment.

3. The splinting device according to claim 2, wherein said first fastener on the interior surface of the wrist attachment and said first fastener on the exterior surface of the wrist attachment are configured to encircle a wrist.

4. The splinting device according to claim 2, wherein said wrist attachment comprises an opening through the wrist attachment from the interior surface of the wrist attachment to the exterior surface of the wrist attachment, wherein said opening is positioned near said first edge and configured to receive a thumb.

5. A splinting device comprising:

a main body having an upper surface and a lower surface, a first side edge, a second side edge, a distal end portion and a proximal end portion;

the main body further comprising a hood at said distal end portion of the main body upending proximally over said upper surface of the main body;

said hood comprising an upper surface and a lower surface, and wherein the lower surface of the hood and the upper surface of the main body define an interior space; a wrist attachment comprising an interior surface and an exterior surface;

a proximal end portion and a distal end portion; a first side edge and a second side edge;

wherein said interior surface of said wrist attachment is connected to the lower surface of the main body at the proximal end of the main body;

a flap comprising an interior surface and an exterior surface; a first side end and a second side end; a top end portion and a bottom end portion;

wherein said bottom end portion of the flap is removably connected to the distal end portion of the wrist attachment.

6. The splinting device according to claim 5, wherein said proximal end portion of the main body comprises one or more elongated slots extending through the main body from the upper surface of the main body to the lower surface of the main body; and said one or more elongated slots are substantially parallel to said lateral and medial edges of the main body.

7. The splinting device according to claim 6, comprising a strap having a first end portion and a second end portion; said threadably engages said one or more elongated slots and said strap is connected to the interior surface of the wrist attachment at said first and second end portions of the strap.

8. The splinting device according to claim 7, wherein said strap slides in said one or more elongated slots allowing the main body to pivot relative to the interior surface of the wrist attachment.

9. The splinting device according to claim 5, wherein said flap comprises a liner on said interior surface of the flap.

10. The splinting device according to claim 5, wherein said upper surface of the main body comprises a liner covering the upper surface of the main body and substantially parallel to the upper surface of the main body.

11. The splinting device according to claim 5, wherein said wrist attachment further comprises a first fastener and second fastener on said exterior surface of the wrist attachment near said first edge; and a first fastener on said interior surface of the wrist attachment near said second edge;

wherein said first fastener on the interior surface of the wrist attachment releasably engages said first fastener on the exterior surface of the wrist attachment.

12. The splinting device according to claim 11, wherein said flap further comprises a second fastener on said interior surface of the flap at said top end portion; and said second fastener releasably engages said second fastener on said exterior surface of the wrist attachment.

13. The splinting device according to claim 12, wherein said second fastener on said interior surface of the flap at said top end portion and said second fastener on said exterior surface of the wrist attachment are configured to cover said main body.

14. The splinting device according to claim 5, wherein said flap further comprises a first fastener on said interior surface of the flap at said bottom end portion; and wherein said first fastener is releasably connected to a third fastener on said exterior surface of the wrist attachment at said distal end.

15. The splinting device according to claim 5, wherein said wrist attachment comprises an opening through the wrist attachment from the interior surface of the wrist attachment to the exterior surface of the wrist attachment, wherein said opening is positioned near said first edge and configured to receive a thumb.

* * * * *